United States Patent
Bussell et al.

(10) Patent No.: US 9,725,388 B2
(45) Date of Patent: *Aug. 8, 2017

(54) DIVALENT ION REMOVAL FROM MONOETHYLENE GLYCOL (MEG) FEED STREAMS

(71) Applicant: Cameron Solutions, Inc., Houston, TX (US)

(72) Inventors: Bryan Anthony Bussell, Sutton (GB); Simon Crawley-Boevey, London (GB); Ankur D. Jariwala, Katy, TX (US)

(73) Assignee: Cameron Solutions, Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/282,495

(22) Filed: Sep. 30, 2016

(65) Prior Publication Data

US 2017/0015612 A1 Jan. 19, 2017

Related U.S. Application Data

(63) Continuation of application No. 14/853,111, filed on Sep. 14, 2015, now Pat. No. 9,469,585, which is a continuation of application No. 14/176,789, filed on Feb. 10, 2014, now Pat. No. 9,133,086.

(51) Int. Cl.

| | | |
|---|---|---|
| *C07C 29/76* | (2006.01) |
| *B01J 14/00* | (2006.01) |
| *B01D 63/00* | (2006.01) |
| *C07C 29/88* | (2006.01) |
| *B01D 61/14* | (2006.01) |
| *B01D 61/16* | (2006.01) |
| *C10L 3/10* | (2006.01) |
| *B01D 9/00* | (2006.01) |
| *B01D 65/02* | (2006.01) |
| *B01J 19/24* | (2006.01) |
| *B01D 63/16* | (2006.01) |
| *C07C 31/20* | (2006.01) |

(52) U.S. Cl.

CPC ............ *C07C 29/76* (2013.01); *B01D 9/0059* (2013.01); *B01D 61/145* (2013.01); *B01D 61/16* (2013.01); *B01D 63/16* (2013.01); *B01D 65/02* (2013.01); *B01J 14/00* (2013.01); *B01J 19/24* (2013.01); *C07C 29/88* (2013.01); *C10L 3/107* (2013.01); *B01D 2311/04* (2013.01); *B01D 2311/08* (2013.01); *B01D 2311/12* (2013.01); *B01D 2311/22* (2013.01); *B01D 2311/2642* (2013.01); *B01D 2315/02* (2013.01); *B01D 2315/04* (2013.01); *B01D 2315/10* (2013.01); *B01D 2321/02* (2013.01); *B01D 2321/04* (2013.01); *B01D 2321/10* (2013.01); *B01D 2321/2058* (2013.01); *B01J 2219/24* (2013.01); *C07C 31/202* (2013.01); *C10L 2290/547* (2013.01); *C10L 2290/548* (2013.01)

(58) Field of Classification Search

CPC .......... C07C 29/76; C07C 29/88; B01J 14/00; B01D 63/00

See application file for complete search history.

(56) References Cited

U.S. PATENT DOCUMENTS

| | | |
|---|---|---|
| 8,329,963 B2 | 12/2012 | Chen |
| 2002/0158014 A1 | 10/2002 | Yamasaki et al. |
| 2012/0253082 A1 | 10/2012 | Morita et al. |

FOREIGN PATENT DOCUMENTS

| | | |
|---|---|---|
| WO | 9839076 | 9/1998 |
| WO | 2005063363 | 7/2005 |
| WO | 2007073204 | 6/2007 |
| WO | 2009017971 | 2/2009 |

*Primary Examiner* — Sikarl Witherspoon

(74) *Attorney, Agent, or Firm* — Gable Gotwals

(57) ABSTRACT

A system and process for removing divalent ions from a MEG feed stream is presented. Embodiments of the system include a chemical treatment tank where chemicals are mixed with the feed stream to form insoluble carbonate and hydroxide salts. The system also includes a solid-liquid separation unit that receives the feed stream from the chemical treatment tank and separates it into a liquids portion containing MEG and a insoluble salts portion. The system may also include washing the insoluble salts portion to remove additional MEG, which is then recycled to a MEG regeneration or reclamation process. The system may also include a dryer that receives waste slurry from the solid-liquid separation unit and dries it to form a solid waste, thereby facilitating its handling, storage, and disposal.

19 Claims, 1 Drawing Sheet

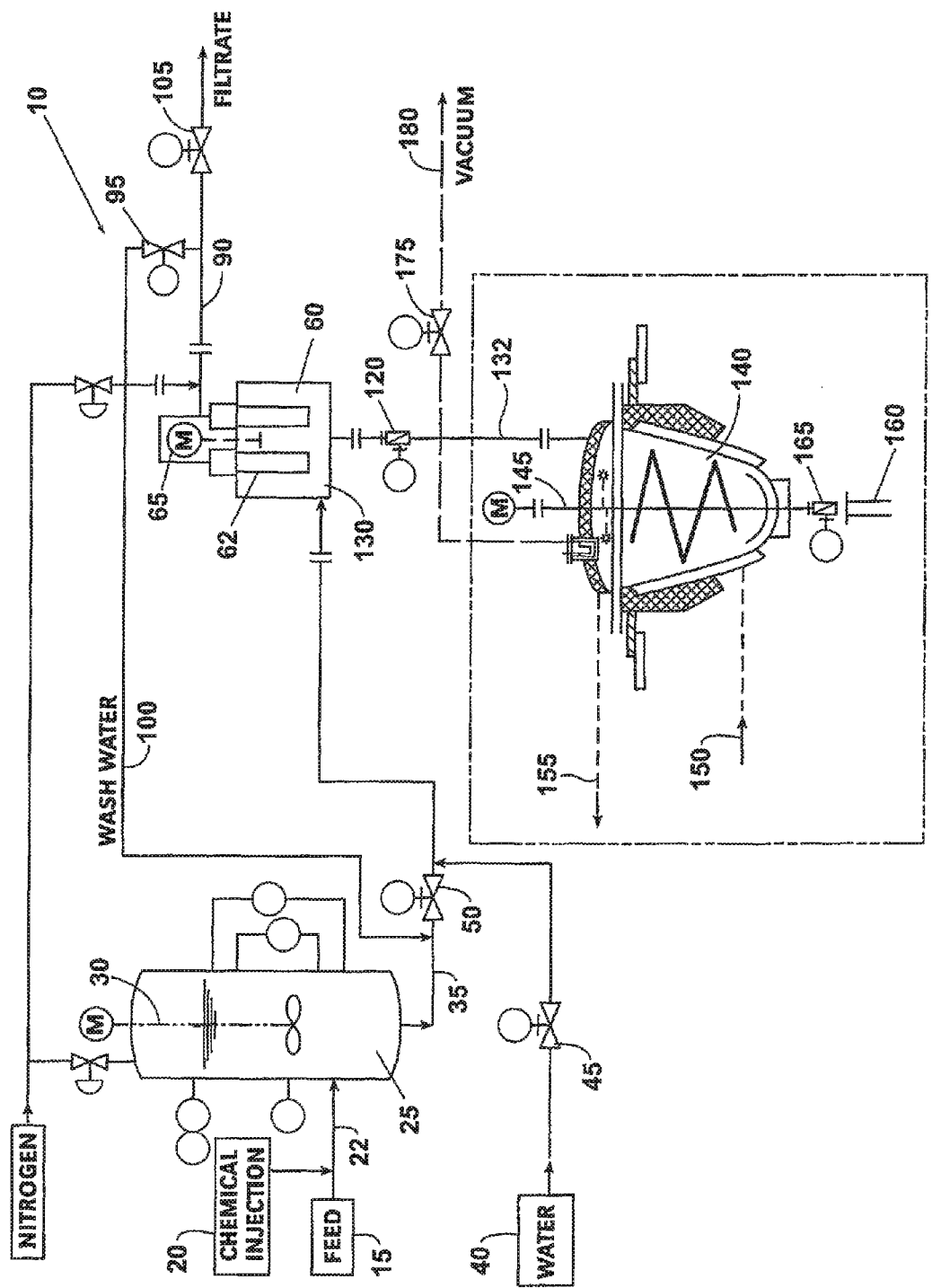

DIVALENT ION REMOVAL FROM MONOETHYLENE GLYCOL (MEG) FEED STREAMS

CROSS REFERENCE TO RELATED APPLICATIONS

This application is a continuation application of U.S. patent application Ser. No. 14/853,111, filed Sep. 14, 2015, which was a continuation of U.S. Pat. No. 9,133,086 (application Ser. No. 14/176,789), the contents of which are hereby incorporated by reference in their entirety.

BACKGROUND

This disclosure relates to systems and processes designed to treat monoethylene glycol (MEG) used in the oil and gas industry, especially in offshore locations, to control the formation of hydrates. More particularly, the disclosure relates to systems and processes that are designed to remove divalent ions from a MEG feed stream.

In the oil and gas industry, MEG is widely used in wellheads and pipelines as a hydrate suppressor to prevent hydrate formation at pipeline conditions. On offshore gas production facilities, where the exposure to lower temperatures in subsea pipelines is significant, MEG is in prevalent use for hydrate inhibition. The lean (dry) MEG is injected in the subsea gas pipeline at or near the wellhead and mixes readily with the produced water. The inhibition process is straightforward, with the MEG decreasing the hydrate formation temperature below the operating temperature and thus preventing hydrate blockage of the pipeline.

The now rich (wet) MEG is then dried so that the MEG can be re-used in hydrate control. However, the lean MEG cannot be recovered by simply distilling the rich MEG and water because the rich MEG is loaded with dissolved salt ions from the produced water, including divalent salts of calcium, magnesium, strontium, and barium. If these salt ions are not removed, they will either precipitate or accumulate in the process equipment, eventually leading to failure of downstream treatment processes.

As an example, if calcium salts are allowed to remain in the MEG feed stream, $Ca(MEG)_4Cl_2$ may form in the flash separator. This compound, which melts at approximately 95° C. (203° F.), forms a hard solid on cooling. This solid may clog pumps, interfere with heat transfer, and inhibit salt removal in downstream treatment processes. In addition, plugged equipment must be taken off-line, which reduces the efficiency and increases the cost of the overall treatment process.

Because some salts of divalent ions are highly soluble, they cannot be removed from MEG feed streams by precipitation. Typically, a chemical reaction is employed to alter the species of the divalent ions into an insoluble form which will precipitate. This precipitate can be removed using a variety of techniques. Conventional removal methods include disk stack centrifuges, filter presses, and candle filters. However, each of these methods has disadvantages. Disk stack centrifuges cause the aeration of the centrate, leading to high oxygen absorption. In addition, because the salts cannot be washed, large amounts of MEG are lost as part of the waste slurry. The high MEG content of the waste slurry also complicates disposal by making the slurry difficult to dry. Filter presses are heavy and require relatively large amounts of space, making them generally unsuitable for offshore applications. Candle filters require chemicals, such as pre-coat or body-aid, and large volumes of gas to dry the filter cake, which add capital and operating costs to their use.

A need exists for systems and processes for removing divalent ions from MEG feed streams in order to improve the efficiency of the MEG reclamation or MEG regeneration process and to prevent the accumulation of salts inside the process equipment. A need also exists for systems and processes that are less expensive, require less space, minimize the use of additional chemicals, reduce the frequency of MEG blowdown, decrease MEG loss by recycling it back to the reclamation or regeneration process, and facilitate the disposal of the waste either as a slurry or as solid waste by means of drying. A need also exists for systems and processes that can be located on the main rich MEG feed stream to the MEG processing plant or on MEG feed streams within the MEG reclamation system (e.g., on a side stream off the flash separator vessel or the recycle loop).

SUMMARY

A system for removing divalent ions from a MEG feed stream is presented. Embodiments of the system include a chemical treatment tank where chemicals are mixed with the feed stream to form insoluble carbonate and hydroxide salts and a membrane-type solid-liquid separation unit that receives the feed stream from the chemical treatment tank and separates it into a filtrate and a retentate. As an example, the solid-liquid separation unit may be a dynamic crossflow filter or a vibrating membrane separation system. The system may also include washing the retentate to remove MEG, which can then be recovered back to the MEG regeneration or reclamation process. The system may also include a dryer that receives the waste slurry from the solid-liquid separation unit and dries it to form a solid waste.

A process for removing divalent ions from a MEG feed stream is also presented. Embodiments of the process includes mixing the feed stream with chemicals in a chemical treatment tank, wherein the divalent ions react with the chemicals to form insoluble carbonate and hydroxide salts; and passing the feed stream from the chemical treatment tank to a membrane-type solid-liquid separation unit, wherein the stream is separated into a filtrate and a retentate that contains the insoluble carbonate and hydroxide salts. The process may also comprise washing the retentate to remove MEG, drying the waste slurry to produce a solid waste, and recycling a portion of the filtrate to the solid-liquid separation unit to backwash the membranes.

The objects of this disclosure include (1) providing a more efficient process to remove divalent ions contained in a MEG feed stream; (2) reducing the amount of MEG lost in the waste slurry; (3) returning the MEG washed from the retentate to the reclamation or regeneration process; (4) facilitating the handling, storage, and disposal of the waste slurry by converting it to solid waste; (5) reducing the amount of time the process equipment is taken off-line for cleaning; (6) providing systems and processes that are less expensive, require less space, and are easier to operate when compared to conventional systems; and (7) providing systems that have a high tolerance to variations in particulate sizes, solids loading, and particle distribution.

BRIEF DESCRIPTION OF THE DRAWING

So that the manner in which the above recited features can be understood in detail, a more particular description may be had by reference to embodiments, some of which are illustrated in the appended drawings, wherein like reference numerals denote like elements. It is to be noted, however, that the appended drawings illustrate various embodiments and are therefore not to be considered limiting of its scope, and may admit to other equally effective embodiments.

The FIGURE presents an embodiment of a process for removing divalent ions from a MEG feed stream, practiced according to embodiments of this disclosure.

ELEMENTS AND NUMBERING USED IN THE DRAWINGS AND THE DETAILED DESCRIPTION

10 Divalent ion removal process
15 Feed stream
20 Chemical injection source
22 Combined chemical and feed stream
25 Chemical treatment tank
30 Mixer
35 Feed stream with insoluble carbonate and hydroxide salts
40 Water source
45 Valve
50 Valve
60 Membrane-type solid-liquid separation unit
62 Membrane stack
65 Motor
90 Filtrate
95 Valve
100 Wash water
105 Valve
120 Valve
130 Retentate
132 Waste slurry
140 Dryer
145 Stirrer
150 Heating medium
155 Heating medium return
160 Solids collection
165 Valve
175 Valve
180 Vacuum line

DETAILED DESCRIPTION

In the following description, numerous details are set forth to provide an understanding of some embodiments of the present disclosure. However, it will be understood by those of ordinary skill in the art that the system and/or methodology may be practiced without these details and that numerous variations or modifications from the described embodiments may be possible.

In the specification and appended claims: the terms "connect", "connection", "connected", "in connection with", and "connecting" are used to mean "in direct connection with" or "in connection with via one or more elements"; and the term "set" is used to mean "one element" or "more than one element". Further, the terms "couple", "coupling", "coupled", "coupled together", and "coupled with" are used to mean "directly coupled together" or "coupled together via one or more elements". As used herein, the terms "up" and "down", "upper" and "lower", "upwardly" and "downwardly", "upstream" and "downstream"; "above" and "below"; and other like terms indicating relative positions above or below a given point or element are used in this description to more clearly describe some embodiments of the disclosure.

As shown in the FIGURE, a system and process involving chemical reaction and solid-liquid separation may be used to remove divalent ions from the MEG feed stream. More particularly, the system and process include the addition of chemicals to the feed stream or directly to the chemical treatment tank to form insoluble carbonate and hydroxide salts that can be separated, along with other particulates, from the feed stream. The system and process also reduce MEG loss by recycling it back to the reclamation or regeneration process and facilitate the disposal of the waste slurry as solid waste.

Embodiments of a divalent ion removal process 10 practiced according to this disclosure begins with the MEG feed stream 15, which is a mixture of produced water and MEG. The MEG feed stream 15 is combined with chemicals from a chemical injection source 20, and the combined chemical and feed stream 22 is routed to a chemical treatment tank 25. Chemicals can also be injected directly into the chemical treatment tank 25. Once in the chemical treatment tank 25, the combined chemical and feed stream 22 is agitated with a mixer 30. The calcium and other divalent ions react with the chemicals to form insoluble carbonate and hydroxide salts. Reaction in the chemical treatment tank 25 may occur at a temperature ranging from approximately 10° C. (50° F.) to approximately 100° C. (212° F.), with a temperature ranging from approximately 50° C. (122° F.) to approximately 85° C. (185° F.). The residence time within the chemical treatment tank 25 is chosen to optimize crystal growth and shape. In some embodiments the residence time may range from approximately five minutes to approximately sixty minutes. In other embodiments the residence time is approximately thirty minutes.

The chemicals combined with the MEG feed stream 15 may include, but are not limited to, potassium carbonate, sodium carbonate, sodium hydroxide, and oxygen scavengers. As an example, an aqueous solution of potassium carbonate may be used to precipitate calcium ions as carbonate. The weight percentage of potassium carbonate in the aqueous solution may range from approximately 15 wt % to approximately 55 wt %; in some embodiments, the weight percentage of potassium carbonate is approximately 47 wt %. As an alternative, an aqueous solution of sodium carbonate may be substituted for potassium carbonate. The weight percentage of sodium carbonate in the aqueous solution may range from approximately 15 wt % to approximately 33 wt %; in some embodiments the weight percentage is approximately 20 wt %. As another example, an aqueous solution of sodium hydroxide may be used to precipitate magnesium ions as hydroxide. The weight percentage of sodium hydroxide in the aqueous solution may range from approximately 10 wt % to approximately 60 wt %; in some embodiments the weight percentage is approximately 50 wt %.

The feed stream with insoluble carbonate and hydroxide salts 35 then exits the chemical treatment tank 25 and flows to a membrane-type solid-liquid separation unit 60 with membrane stack 62. Flow from the chemical treatment tank 25 to the solid-liquid separation unit 60 is controlled through a valve 50 by pressure or by a pump (not shown). The type of solid-liquid separation unit 60 may include, but is not limited to, a dynamic crossflow filter or vibrating membrane separation system. In a dynamic crossflow filter, the majority of the stream is passed under pressure through ceramic ultrafiltration membranes arranged as rotating disks inside a pressure vessel. The constantly rotating disks help to self-clean the surface of the membranes, which prevents them from becoming overly fouled. The ultrafiltration membranes within the dynamic crossflow filter are interchangeable. A vibrating membrane separation system uses high-speed vibration of the membrane structure to break down the solids fouling layer that accumulates on the membrane surface. Membrane vibration or rotation is generally motor 65 driven.

Regardless of the type chosen, the separation unit 60 is able to tolerate variations in particulate sizes, solids loadings, and particle distribution. As an example, the pore size in a membrane-type separator is small enough to remove other particulates, such as pipe scale, in addition to the solids precipitated within the chemical treatment tank 25. In addition, because the separation unit 60 is filled with liquid during operation, there is minimal contact of the MEG with the purge gas. This prevents oxygenation of the MEG, thereby minimizing degradation of the MEG and the corrosion of process equipment. The separation unit 60 is also compact, easily accessible for maintenance and repair, and incorporates clean-in-place systems to remove fouling from the membrane stack 62.

The separation unit 60 divides the feed stream with insoluble carbonate and hydroxide salts 35 into a filtrate 90 containing MEG and a retentate 130 that contains the insoluble salts. The filtrate 90, which contains primarily of MEG and water, exits the top of the solid-liquid separation unit 60 after passing through the membrane stack 62 and then discharges through valve 105 to downstream treatment processes such as MEG regeneration or reclamation. A portion of the filtrate 90 may be used periodically to backwash the membranes in the separation unit 60. As insoluble salts accumulate in the retentate 130, it thickens to a point where it can be removed from the solid-liquid separation unit 60 as a waste slurry 132.

Before removal from the solid-liquid separation unit 60, the retentate 130 may be washed to remove MEG and to minimize contaminants in the waste slurry 132. A primary advantage of the retentate wash is to recover MEG back to the process, thereby minimizing MEG losses from the system. This washing involves stopping the flow of the feed stream with insoluble carbonate and hydroxide salts 35 from the chemical treatment tank 25 to the separation unit 60. The solid-liquid separation unit 60 is isolated by closing the valve 50 from the chemical treatment tank 25 and the valve 105 on the discharge line for filtrate 90. Valve 45 is opened, which allows water from the water source 40 to flow to the solid-liquid separation unit 60. Water then flows through the separation unit 60 in the same direction as that of normal flow. MEG remaining in the retentate is carried with the water through the membrane stack 62 and out of the separation unit 60 through the return line for wash water 100 and back to chemical treatment tank 25. When the retentate 130 has been sufficiently washed, valves 50 and 95 are closed to isolate the separation unit 60 and valve 120 is opened. As the separation unit 60 operates under pressure, the opening of valve 120 causes the retentate to evacuate the separation unit 60. If the retentate is being discharged to a local heater, no further action may be required. However, if the retentate is being discharged to a remote location for further treatment, valve 45 can be opened to provide water to aid in the transportation of the slurry.

The MEG that is removed from the retentate 130 is recycled to the MEG regeneration or reclamation process, thereby reducing the amount of MEG lost in the waste slurry 132 and improving the efficiency of the overall treatment process. In addition, if the MEG is not removed, drying the waste slurry 132 may become impeded due to decomposition of the MEG. This decomposition can result in a sticky fouling paste, even when dried at low temperature under vacuum, that clogs equipment, is difficult to handle, and prevents the storage and treatment of the slurry as solid waste. Drying the waste slurry 132 at atmospheric pressure at the corresponding higher temperature can increase the rate of MEG decomposition, further complicating waste handling and disposal.

This waste slurry 132 may optionally travel to a dryer 140, with the flow of the waste slurry 132 controlled by valve 120. The dryer may be a helix dryer or a paddle dryer. Within the dryer 140, the waste slurry 132 is stirred by stirrer 145 and heated by a heating medium 150 that enters near the base of the dryer 140, flows upward, and exits through a heating medium return 155 located near the top of the dryer 140. The dryer 140 operates under a vacuum through vacuum line 180, which is regulated by valve 175. Drying temperatures depend on the operating pressure in the dryer. Operating under vacuum may reduce the boiling temperature of the waste slurry 132, thereby preventing the baking of solids on the metal surfaces of the dryer 140, minimizing the degradation of any residual MEG or hydrocarbons in the waste slurry 132, and minimizing operator exposure to high temperatures. The dryer 140 may be provided with clean-in-place systems to facilitate periodic maintenance. The dried solids exit the dryer 140 and are sent to solids collection 160 by opening valve 165. The form of the dried solids may include, but is not limited to, granules, pellets, or powder.

An advantage of the present invention is that it removes divalent ions from MEG feed streams in order to improve the efficiency of the MEG reclamation or MEG regeneration process and to prevent the accumulation of salts inside the process equipment. Another advantage is that the retentate may be washed, with the recovered MEG being returned to the reclamation or regeneration process. As an example, the MEG lost from the present system is less than ten percent of the MEG lost in a disk stack centrifuge. Removing the MEG from the retentate also facilitates the drying of the waste slurry and the production of a solid waste that is easier to handle, transport, and store. In addition, the present system has a compact design that is particularly good for offshore installation, prevents the carryover of particulates into the filtrate and downstream treatment processes, should not require degasification of the filtrate, and is easy to clean, either manually or through its clean-in-place systems.

While a system and process for removing divalent ions from a feed stream containing MEG have been described in detail, a person of ordinary skill in the art understands that certain changes can be made in the arrangement of process and type of components used in the system and process without departing from the scope of the following claims.

Although the preceding description has been described herein with reference to particular means, materials and embodiments, it is not intended to be limited to the particulars disclosed herein; rather, it extends to all functionally equivalent structures, methods, and uses, such as are within the scope of the appended claims.

What is claimed is:
1. A system for removing divalent ions from a feed stream having MEG mixed with produced water, the system comprising:
 a chemical treatment tank arranged to receive the feed stream and react chemicals mixed with the feed stream to form insoluble carbonate and hydroxide salts; and
 a solid-liquid separation unit arranged to receive the reacted feed stream from the chemical treatment tank and separate the reacted feed stream into a liquids portion and an insoluble salts portion;

a return line arranged to receive wash water used to wash the insoluble salts portion and return the wash water to the chemical treatment tank.

2. A system according to claim 1 wherein the chemical treatment tank has a temperature ranging from approximately 10° C. (50° F.) to approximately 100° C. (212° F.).

3. A system according to claim 1 wherein the chemical treatment tank has a temperature ranging from approximately 50° C. (122° F.) to approximately 85° C. (185° F.).

4. A system according to claim 1 wherein the chemical treatment tank has a residence time ranging from approximately five minutes to approximately sixty minutes.

5. A system according to claim 4 wherein the residence time is approximately thirty minutes.

6. A system according to claim 1 wherein the chemicals that react with the divalent ions to form the insoluble carbonate and hydroxide salts are chosen from the group consisting of potassium carbonate, sodium carbonate, and sodium hydroxide.

7. A system according to claim 1 wherein oxygen scavengers are added to the chemical treatment tank.

8. A system according to claim 1 wherein the solid-liquid separation unit includes a dynamic crossflow filter.

9. A system according to claim 1 where in solids-liquid separation unit includes a vibrating membrane separation system.

10. A system according to claim 1 wherein the solid-liquid separation unit includes one or more membranes.

11. A system according to claim 10 wherein the solid-liquid separation unit has a clean-in-place system to remove fouling from the one or more membranes in the separation unit.

12. A system according to claim 1 wherein the MEG that is removed from the insoluble salts portion is recovered to a MEG regeneration or reclamation process.

13. A system according to claim 1 wherein a portion of the liquids portion from the solid-liquid separation unit is used to backwash membranes in the separation unit.

14. A system according to claim 1 further comprising a dryer arranged to receive waste slurry from the solid-liquid separation unit and dry the waste slurry to form a solid waste.

15. A process for removing divalent ions from a feed stream having MEG mixed with produced water, the process comprising the steps of:

reacting the divalent ions in the feed stream with chemicals inside a chemical treatment tank to form insoluble carbonate and hydroxide salts;

passing the reacted feed stream from the chemical treatment tank to a solid-liquid separation unit, wherein the stream is separated into a liquids portion and an insoluble salts portion;

washing the insoluble salts portion with wash water; and routing the wash water to the chemical treatment tank.

16. A process according to claim 15 wherein the chemicals include at least one chemical chosen from the group consisting of potassium carbonate, sodium carbonate, sodium hydroxide, and an oxygen scavenger.

17. A process according to claim 15 further comprising the step of drying waste slurry to produce a solid waste.

18. A process according to claim 15 further comprising the step of returning a portion of the liquids portion to the solid-liquid separation unit as backwash water.

19. A process according to claim 15 further comprising the step of routing the MEG that is removed from the insoluble salts portion to a MEG regeneration or reclamation process.

* * * * *